United States Patent
Hutchinson

(10) Patent No.: US 10,748,016 B2
(45) Date of Patent: Aug. 18, 2020

(54) IN-VEHICLE MONITORING

(71) Applicant: Oxehealth Limited, Oxford (GB)

(72) Inventor: Nicholas Dunkley Hutchinson, Oxford (GB)

(73) Assignee: OXEHEALTH LIMITED, London (GB)

( * ) Notice: Subject to any disclaimer, the term of this patent is extended or adjusted under 35 U.S.C. 154(b) by 185 days.

(21) Appl. No.: 15/961,279

(22) Filed: Apr. 24, 2018

(65) Prior Publication Data

US 2018/0307927 A1 Oct. 25, 2018

(30) Foreign Application Priority Data

Apr. 24, 2017 (GB) .................................. 1706449.4

(51) Int. Cl.
*G06K 9/00* (2006.01)
*A61B 5/00* (2006.01)
(Continued)

(52) U.S. Cl.
CPC ........ *G06K 9/00845* (2013.01); *A61B 5/7207* (2013.01); *G06K 9/00744* (2013.01);
(Continued)

(58) Field of Classification Search
CPC .......... G06T 7/20; G06T 7/248; G06T 7/262; G06T 2207/30004; G06T 2207/30104;
(Continued)

(56) References Cited

U.S. PATENT DOCUMENTS 8,855,384 B2   10/2014   Kyal et al. .................... 382/128
8,965,090 B1   2/2015    Khachaturian et al. .....................
                                                          G01K 13/004
(Continued)

FOREIGN PATENT DOCUMENTS

EP   0615245 A2   9/1994   ............. G11B 27/28
EP   0919184 A1   6/1999   ............... A61B 5/08
(Continued)

OTHER PUBLICATIONS

Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.

(Continued)

*Primary Examiner* — Andrew W Johns
(74) *Attorney, Agent, or Firm* — Harness, Dickey & Pierce, P.L.C.

(57) ABSTRACT

In a method of video monitoring of a subject, for example a driver of a vehicle, the video image is motion compensated by image registration techniques so that the subject's position in each frame of the video image is stable. A region of interest is defined on the skin of the subject and used to obtain a PPG signal. To compensate for variations in illumination of the subject caused by the subject's movement in the vehicle, the parameters of the calculated motion transformation used in the image registration are used to form an illumination model representing how the illumination of the subject would have changed because of the subject's motion. The illumination model is a linear or quadratic function fitted to the image intensity in the region of interest. Residuals between the fitted model and the image intensity form an illumination-compensated signal in which the photoplethysmographic signal is more clearly present. The (Continued)

illumination-compensated signal is analysed to obtain a PPG signal and from this estimates of one or more vital signs such as heart rate or breathing rate are obtained.

13 Claims, 6 Drawing Sheets

(51) Int. Cl.
| | | |
|---|---|---|
| *G06T 7/00* | (2017.01) | |
| *G06T 7/246* | (2017.01) | |
| *G06T 5/00* | (2006.01) | |
| *A61B 5/18* | (2006.01) | |
| *A61B 5/024* | (2006.01) | |

(52) U.S. Cl.
CPC ............ *G06T 5/003* (2013.01); *G06T 7/0016* (2013.01); *G06T 7/248* (2017.01); *A61B 5/0077* (2013.01); *A61B 5/02416* (2013.01); *A61B 5/18* (2013.01); *A61B 5/6893* (2013.01); *A61B 5/7485* (2013.01); *G06K 9/00261* (2013.01); *G06T 2207/10016* (2013.01); *G06T 2207/20201* (2013.01); *G06T 2207/30076* (2013.01); *G06T 2207/30196* (2013.01); *G06T 2207/30268* (2013.01)

(58) Field of Classification Search
CPC ...... G06T 2207/30196; G06K 9/00261; G06K 9/00362; G06K 9/00744; G06K 9/00845; G06K 9/4661; A61B 5/0077; A61B 5/0205; A61B 5/02416; A61B 5/18; A61B 5/6893
See application file for complete search history.

(56) References Cited

U.S. PATENT DOCUMENTS

| | | | |
|---|---|---|---|
| 9,036,877 B2 | 5/2015 | Kyal et al. ............ | A61B 5/7225 |
| 10,034,979 B2 | 7/2018 | Bechtel et al. ........ | A61M 5/172 |
| 10,292,662 B2 | 5/2019 | Kirenko ............... | A61M 5/7278 |
| 2002/0106709 A1 | 8/2002 | Potts et al. ........................ | 435/14 |
| 2002/0180870 A1 | 12/2002 | Chen .......................... | 348/207.1 |
| 2003/0138149 A1 | 7/2003 | Iizuka et al. .................. | 382/236 |
| 2003/0228032 A1 | 12/2003 | Rui et al. ....................... | 382/103 |
| 2005/0197590 A1 | 9/2005 | Osorio et al. .................. | 600/544 |
| 2006/0058618 A1 | 3/2006 | Nishiura ....................... | 600/407 |
| 2007/0156060 A1 | 7/2007 | Cervantes ..................... | 600/534 |
| 2007/0195931 A1 | 8/2007 | Ohishi ........................ | 378/98.2 |
| 2008/0292151 A1 | 11/2008 | Kurtz et al. ................... | 382/128 |
| 2009/0216499 A1 | 8/2009 | Tobola et al. .................. | 702/190 |
| 2010/0049064 A1 | 2/2010 | Bodmer et al. ................ | 600/508 |
| 2010/0074475 A1 | 3/2010 | Chouno ....................... | 382/107 |
| 2010/0298656 A1 | 11/2010 | McCombie et al. ............ | 600/301 |
| 2011/0046498 A1 | 2/2011 | Klap et al. .................... | 600/534 |
| 2011/0150274 A1 | 6/2011 | Patwardhan et al. ......... | 382/103 |
| 2011/0251493 A1 | 10/2011 | Poh et al. ..................... | 600/477 |
| 2011/0311143 A1 | 12/2011 | Cennini et al. ............... | 382/191 |
| 2012/0141000 A1 | 6/2012 | Jeanne et al. ................. | 382/128 |
| 2012/0213405 A1 | 8/2012 | Saski .......................... | 382/103 |
| 2012/0242819 A1 | 9/2012 | Schamp ......................... | 348/78 |
| 2013/0138009 A1 | 5/2013 | Nierenberg et al. ........... | 600/544 |
| 2013/0324875 A1 | 12/2013 | Mestha et al. ................. | 600/534 |
| 2014/0003690 A1 | 1/2014 | Razeto et al. ................. | 382/131 |
| 2014/0023235 A1 | 1/2014 | Cennini et al. ..... | G06K 9/00362 |
| 2014/0037163 A1 | 2/2014 | Kirenko et al. ...... | G06T 7/0038 |
| 2014/0037166 A1 | 2/2014 | De Haan et al. ..... | G06T 7/0012 |
| 2014/0236036 A1* | 8/2014 | de Haan et al. ..... | A61B 5/1135 600/534 |
| 2014/0276099 A1 | 9/2014 | Kirenko et al. ... | A61B 5/02416 |
| 2014/0276104 A1 | 9/2014 | Tao et al. ............ | A61B 5/7239 |
| 2014/0334697 A1 | 11/2014 | Kersten et al. ...... | A61B 5/0816 |
| 2014/0371599 A1 | 12/2014 | Wu et al. ............. | A61B 5/4082 |
| 2014/0371635 A1 | 12/2014 | Shinar et al. ........ | A61B 5/1102 |
| 2014/0378842 A1 | 12/2014 | Xu et al. ............. | A61B 5/0077 |
| 2015/0005646 A1 | 1/2015 | Balakrishnan et al. ...... A61B 5/02438 |
| 2015/0063708 A1 | 3/2015 | Sripadarao et al. .. | G06T 7/0085 |
| 2015/0148687 A1 | 5/2015 | Kitajima et al. ... | A61B 5/02427 |
| 2015/0208987 A1* | 7/2015 | Shan et al. .......... | A61B 5/7207 600/473 |
| 2015/0221069 A1 | 8/2015 | Shaburova et al. .... | G06T 5/005 |
| 2015/0250391 A1 | 9/2015 | Kyal et al. ............ | A61B 5/024 |
| 2015/0363361 A1 | 12/2015 | Kniazev .................. | G06F 17/16 |
| 2016/0106340 A1 | 4/2016 | Mestha et al. ....... | A61B 5/0816 |
| 2016/0125260 A1 | 5/2016 | Huang et al. ......... | G06K 9/4671 |
| 2016/0132732 A1 | 5/2016 | Gunther et al. ... | G06K 9/00771 |
| 2016/0220128 A1 | 8/2016 | Den Brinker et al. ...... A61B 5/02055 |
| 2016/0253820 A1 | 9/2016 | Jeanne et al. ........... | G06T 7/204 |
| 2016/0310067 A1 | 10/2016 | Heinrich et al. ..... | A61B 5/4815 |
| 2017/0007185 A1 | 1/2017 | Lin et al. ............... | A61B 5/721 |
| 2017/0042432 A1 | 2/2017 | Adib et al. ............ | A61B 5/0255 |
| 2017/0224256 A1 | 8/2017 | Kirenko ............... | A61B 5/1128 |
| 2017/0238805 A1* | 8/2017 | Addison et al. ..... | A61B 5/0205 |
| 2017/0238842 A1 | 8/2017 | Jacquel et al. ....... | A61B 5/1032 |
| 2018/0085010 A1 | 3/2018 | Jones et al. ......... | A61B 5/02108 |
| 2018/0279885 A1 | 10/2018 | Bulut ................... | A61B 5/0205 |
| 2019/0000391 A1 | 1/2019 | De Haan et al. .... | A61B 5/7214 |
| 2019/0267040 A1 | 8/2019 | Ikeda et al. .......... | G11B 27/034 |

FOREIGN PATENT DOCUMENTS

| | | | |
|---|---|---|---|
| EP | 1571594 A2 | 9/2005 | ............. G06T 7/40 |
| EP | 2767233 A1 | 8/2014 | ............. A61B 5/113 |
| EP | 2976998 A1 | 1/2016 | ............. A61B 5/024 |
| EP | 2988274 A2 | 2/2016 | ............. G06T 7/20 |
| EP | 3207862 A1 | 8/2017 | ............. A61B 5/00 |
| JP | 2011130996 A | 7/2011 | ............. A61B 5/11 |
| WO | WO-2010/100593 A1 | 9/2010 | ............. G06K 9/00 |
| WO | WO-2010/115939 A2 | 10/2010 | ........... A61B 5/0476 |
| WO | WO-2011021128 A2 | 2/2011 | ............. G06K 9/00 |
| WO | WO-13/027027 A2 | 2/2013 | ........... A61B 5/0205 |
| WO | WO-2014125250 A1 | 8/2014 | ............. G06T 7/00 |
| WO | WO-2014131850 A1 | 9/2014 | ............. A61B 5/11 |
| WO | WO-2014140994 A1 | 9/2014 | ............. A61B 5/00 |
| WO | WO-2015049150 A1 | 4/2015 | ............. A61B 5/00 |
| WO | WO-2015055709 A1 | 4/2015 | ............. A61B 5/00 |
| WO | WO-2015/078735 A1 | 6/2015 | ............. A61B 5/11 |
| WO | WO-2015/091582 A1 | 6/2015 | ............. A61B 5/00 |
| WO | WO-2016092290 A1 | 6/2016 | ............. A61B 5/0295 |
| WO | WO-2016094749 A1 | 6/2016 | ............. A61B 5/00 |
| WO | WO-2016159151 A1 | 10/2016 | ........... A61B 5/0245 |
| WO | WO-2017125743 A1 | 7/2017 | ............. G06K 9/00 |
| WO | WO-2017125744 A1 | 7/2017 | ............. A61B 5/08 |
| WO | WO-2017125763 A1 | 7/2017 | ............. A61B 5/024 |

OTHER PUBLICATIONS

Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding application No. 18168310.3-1115 dated Oct. 1, 2018.
Search Report regarding United Kingdom Patent Application No. GB1706449.4, dated Oct. 25, 2017.
Kumar-DistancePPG: Robust non-contact vital signs monitoring using a camera, Optical Society of America (2015).
Pisani-Real-time Automated Detection of Clonic Seizures in Newborns, Clinical Neurophysiology 125 (2014) 1533-1540.
Verkruysse-Remote Plethysmographic Imaging using Ambient Light, Optics Express (Dec. 22, 2008) vol. 16, No. 26.
Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.
Qiang Zhu et al, "Learning a Sparse, Corner-Based Representation for Corner-Based Representation for Time-varying Background Modeling", Computer Vision, 2005. ICCV 2005. Tenth IEEE

(56) References Cited

OTHER PUBLICATIONS

International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.
Konstantinos Avgerinakis et al, "Activity detection and recognition of daily living events", Proceedings of the 1st ACM International Workshop on Multimedia Indexing and Information Retrieval for Healthcare, MIIRH '13, Oct. 22, 2013 (Oct. 22, 2013), pp. 1-7.
Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.
Yu Sun et al,"Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.
Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.
Hisato Aota et al, "Extracting objects by clustering of full pixel trajectories", Signal Processing and Multimedia Applications (SIGMAP), Proceedings of the 2010 International Conference On, IEEE, Jul. 26, 2010 (Jul. 26, 2010), pp. 65-72.
Shandong Wu et al, "A hierarchical motion trajectory signature descriptor", 2008 IEEE International Conference on Robotics and Automation. The Half-Day Workshop on: Towards Autonomous Agriculture of Tomorrow, IEEE—Piscataway, NJ, USA, Piscataway, NJ, USA, May 19, 2008 (May 19, 2008), pp. 3070-3075.
Search Report for GB Application No. 1618828.6, dated Mar. 31, 2017.
International Prelim. Report on Patentability for PCT/GB2017/053343, dated Jan. 4, 2018; ISA/EP.
International Search Report for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Application No. PCT/GB2017/052779 dated Mar. 19, 2019.
International Search Report for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1061143.9, dated Mar. 30, 2016.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
International Search Report for PCT/GB2017/050126, ISA/EP, Rijswijk, NL, dated Apr. 20, 2017.
Written Opinion of the ISA for PCT/GB2017/050126, ISA/EP, Rijswijk, NL, dated Apr. 20, 2017.
UK IPO Search Report for GB priority application 1601217.1, Newport, South Wales, dated Jul. 25, 2016.
European Search Report regarding Application No. EP 19 15 8085 dated Jul. 10, 2019.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Search Report of UKIPO regarding Application No. GB1900033.0 dated Jun. 13, 2019.
British Search Report regarding Application No. 1900034.8 dated Jun. 13, 2019.
Extended EP Search Report regarding Application No. 19220090.5 dated Feb. 24, 2020.

* cited by examiner

IN-VEHICLE MONITORING

CROSS-REFERENCE TO RELATED APPLICATIONS

This application claims the benefit of Great Britain Patent Application No. 1706449.4, filed Apr. 24, 2017. The entire disclosure of the above application is incorporated herein by reference.

FIELD

The present invention relates to improvements in or relating to in-vehicle monitoring and in particular to video monitoring of the operator of a vehicle to obtain an estimate of a vital sign, such as a heart rate or breathing rate, of the operator.

BACKGROUND

Video monitoring of vehicle operators, such as car, truck or train drivers, aeroplane pilots and so on has been of interest for many years. As well as simply recording video of the operator to monitor their behaviour and state of alertness, various systems have been proposed for automatically detecting deteriorations in alertness caused by, for example, health problems or drowsiness. The results may be stored or, preferably, an alarm can be generated to alert the operator or the controls of the vehicle may be operated to bring the vehicle to a safe condition.

More recently, proposals have been made for analysing video images of human subjects and in particular analysing variations in skin tone in the image to detect a photoplethysmographic (PPGi) signal in the image representing the heart rate of the subject. Such a PPGi signal also carries a breathing rate modulation, allowing an estimate of both the heart rate and breathing rate in some circumstances. The video image of the subject can also be frequency analysed to detect movements in the expected frequency range for breathing rate or heart rate (such as movements of the chest or shoulders), and an estimate of breathing rate obtained from such movements. Such techniques are described in WO-A-2013/027027.

A problem, however, is that most demonstrations of the estimate of a subject's vital signs from video images are performed in very controlled conditions. Usually lighting is carefully arranged to be stable and even and the subject is requested to remain still during the period of video image capture. While the prior art demonstrates that it is possible to obtain reasonable estimates of heart rate and breathing rate in such conditions, in practical situations, particularly in moving vehicles, conditions are far from ideal and it is extremely difficult to obtain reasonable estimates of a subject's vital signs. In particular, illumination levels often vary spatially, while the motion of the vehicle induces motion in the subject, such that the level of illumination reaching a given region of the patient's skin varies temporally; even if the illumination levels relative to the car are temporally constant.

PPGi analysis techniques normally rely on the definition of one or more regions of interest on skin areas of the subject. The colour and/or luminance values from the regions of interest is used to provide a signal from which the PPG signal is to be obtained. However if the region of interest moves to a different skin region of the subject, this will introduce noise into the signal. Therefore it has been proposed to perform image registration on the video image so that the subject's position in the image is consistent (while the background appears to move), allowing the region of interest to be positioned at the same place within each image frame. However because the subject is moving within the spatially varying illumination field within the vehicle, although the subject's position in the image frame is stable, the brightness of the subject will seem to vary. Thus the movement of the subject will cause a variation in illumination which contaminates the image signal from which the PPG signal is to be obtained.

The same problem of a subject's movement causing a variation in illumination occurs in any video monitoring situation where the subject is moving and the illumination field is not completely spatially uniform.

An object of the invention is to provide for a method of processing a video image of a human subject to allow estimation of a vital sign, such as heart rate or breathing rate of the subject, which allows reduction of artifacts caused by motion-induced illumination variations and thus provides a better estimate of the vital sign.

SUMMARY

In more detail the present invention provides a method of processing sequence of image frames forming a video image of a human subject to estimate a vital sign of the subject comprising the steps of: analysing the video image to obtain a motion transformation whose parameters represent the movement of the subject; defining at least one region of interest on the subject in the video image and obtaining a signal representing the image intensity in the at least one region of interest; obtaining a predicted illumination signal by fitting a function of the motion transformation parameters to the signal representing the image intensity; obtaining a residuals signal representing the difference between the signal representing the image intensity and the predicted illumination signal after said fitting; and analysing the residuals signal to obtain an estimate of at least one vital sign of the subject.

The step of analysing the video image to obtain a motion transformation may comprise performing a motion correction process, such as image registration, which produces a motion corrected video image and the motion transformation.

Alternatively, the region of interest is defined in the video image before the step of analysing the video image to obtain a motion transformation, and the step of analysing the video image to obtain a motion transformation comprises tracking the region of interest through the sequence of image frames. Thus the varying position of the region of interest represents the motion transformation.

The motion transformation in general has at least two and no more than eight parameters. In one example the motion transformation is a projective transformation, for example which returns eight parameters, being the three orthogonal translation directions of the subject, rotations of the subject around three orthogonal axes, and two parameters representing camera position. The transformation may be an affine transformation for example. In another example the motion transformation may have parameters corresponding to the position of the region of interest, e.g. the position of the vertices of the region of interest, or some other feature of the region of interest. For a triangular region of interest there would therefore be six parameters—corresponding to the x,y coordinates of each vertex. This is then equivalent to an affine transformation; accounting for x y translation, tilt forwards, tilt sideways, in plane rotation and scale changes (moving towards or away from the camera).

The step of fitting the function of the motion transformation parameters to the image intensity signal may comprise simple linear regression fitting, or quadratic regression fitting.

There may be one or more regions of interest defined on the subject, preferably on automatically detected areas on the subject's skin. Such areas may be automatically detected by virtue of detecting skin tone or recognising the shape of the subject in the image, or by defining them in relation to image features automatically detected and tracked through the video image.

An intensity representative signal may be formed for each region of interest as an average or sum of pixel values in that region. It may be based on the luminance of the image or a signal derived from one or more colour channels of the video signal.

For a single vital sign, e.g. heart rate, estimate the method starts by taking n adjacent frames. The motion transformation is then obtained, offering 8 transformation signals, each of length n. Suppose a total of m regions of interest are defined. Then they will provide m intensity signals, each of length n. Each of these signals is then fitted against the 8 transformation signals. This provides m residual signals, each of length n. These residual signals may then be combined into a final signal of length n from which the vital sign, e.g. heart rate, is extracted, or each signal can be used to extract an estimate and a signal quality index, with the estimates then being combined as a function of their signal quality indices.

The image intensity signal preferably contains a PPG signal relating to variations in the transmissivity or reflectivity of the skin as the amount of oxygenated blood in the skin capillaries varies with heart beat.

In one application of the invention the video image is the image of a subject in a vehicle, such as the operator of the vehicle, e.g. driver or pilot. However, the invention is applicable to other monitoring situations where the subject is in motion in a non-uniform illumination field such as a subject sitting or standing with their head unsupported.

Another aspect of the invention provides an apparatus for processing a video image in accordance with the method above. Such an apparatus may include an image processor and a data store and/or display for storing the results and/or displaying them. In the context of operator monitoring the apparatus may include an alarm and/or an interface to the controls of the vehicle or machine to allow it to be brought into a safe condition in the event of the subject's vital signs being sufficiently abnormal.

The invention also extends to a video monitoring system comprising a video camera and such an image processing apparatus, and to a vehicle having such a video monitoring system installed therein.

The method of the invention may be embodied in computer software which when executed on a programmed computer system processes captured video images in accordance with the method above to obtain and output an estimate of the vital sign of the subject. Thus the invention extends to computer-readable media storing such computer software and to computer systems programmed with such software.

DRAWINGS

FIG. 1 schematically illustrates a vehicle including an embodiment of the invention;

FIG. 2 schematically illustrates the main parts of a video monitoring system in accordance with an embodiment of the invention;

Figure 7A:
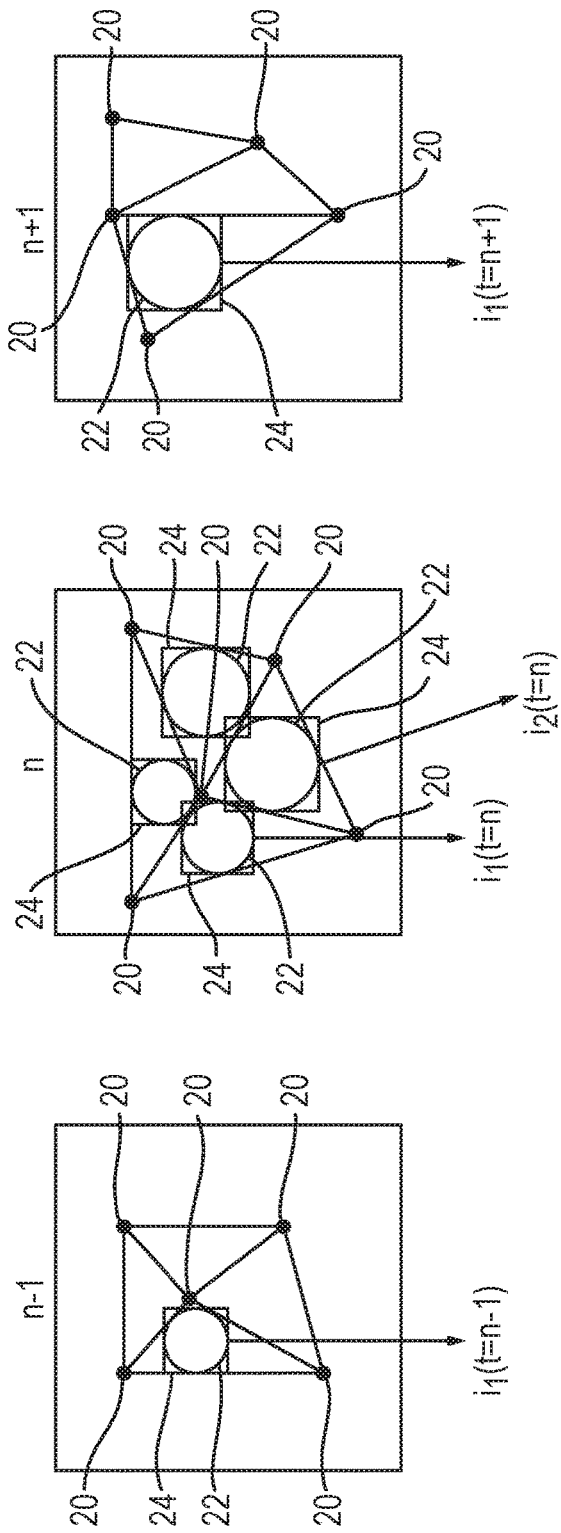
Figure 7B:
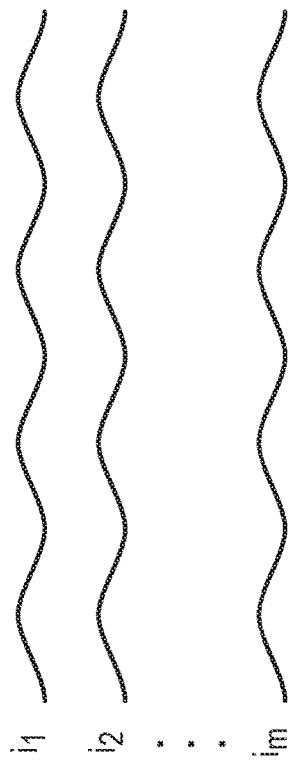
Figure 8:
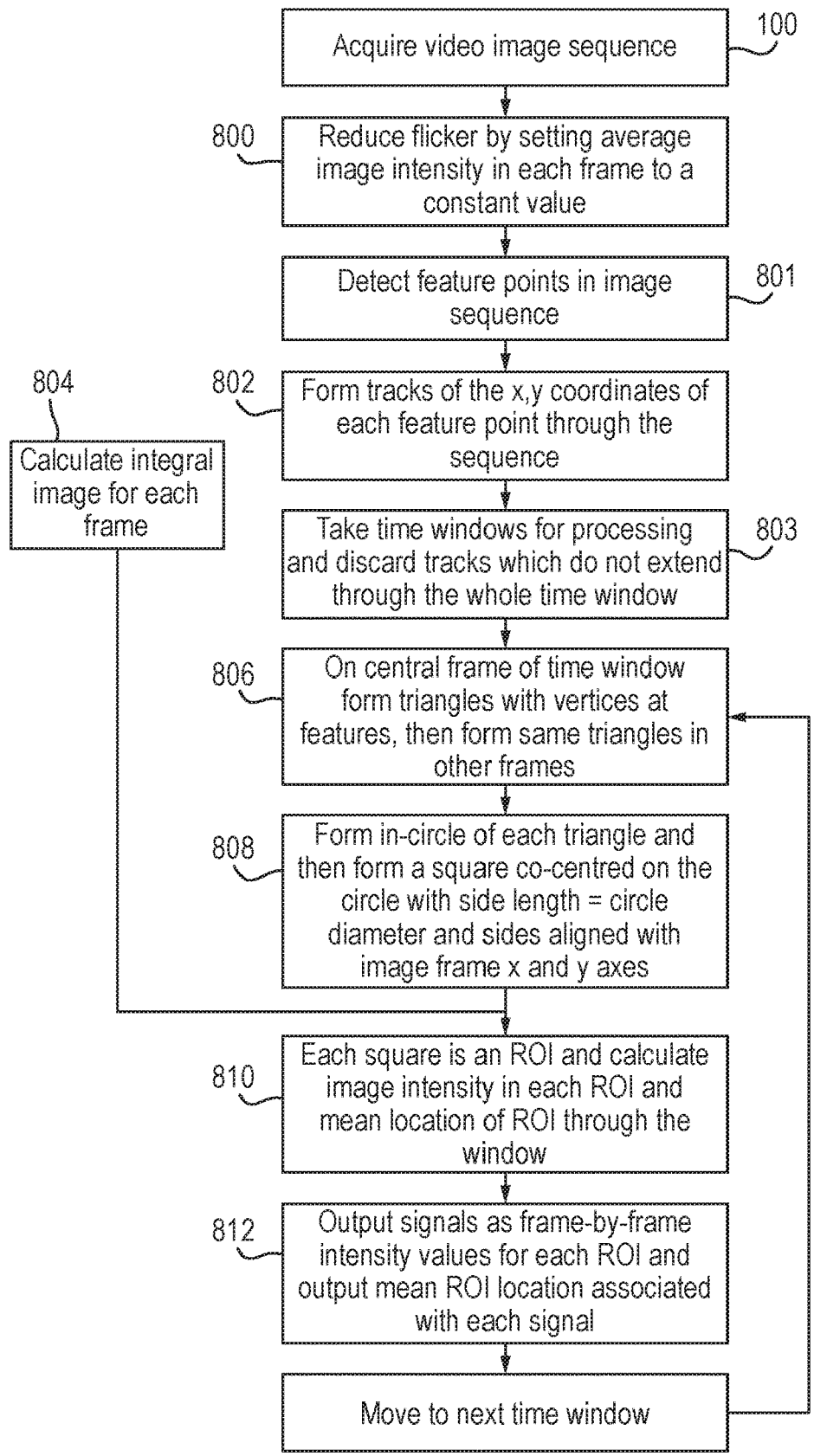

FIGS. 7(A) and 7(B) illustrate regions of interest and resulting signals according to the alternative embodiment of the invention FIG. 8 is a flow diagram illustrating a way of defining regions of interest for the alternative embodiment of the invention.

DETAILED DESCRIPTION

Figure 1:
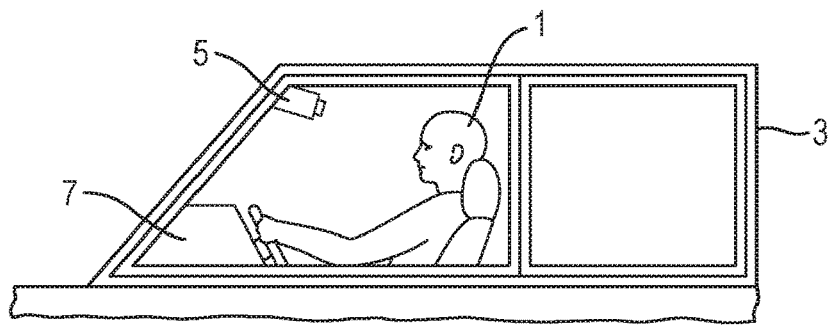

FIG. 1 schematically illustrates a vehicle 3 occupied by an operator 1 who is the subject of a video image captured by video camera 5. The video camera 5 may be a standard colour or monochrome digital video camera producing a monochrome or colour digital video signal consisting of a sequence of image frames, typically at a frame rate of 20 frames per second for example.

Figure 2:
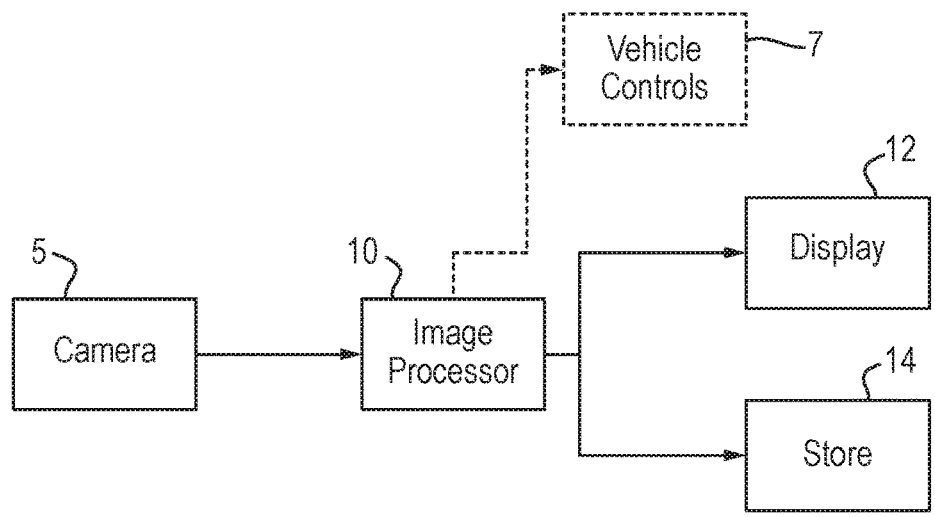

As shown in FIG. 2, the camera 5 supplies its output (a video image) to an image processor 10 which processes the video image as will be described later to obtain an estimate of a vital sign of the subject 1. This estimate may be output via a display 12 and/or recorded in a data store 14. Optionally the image processor may also supply an output to the vehicle controls 7 if it is desired to provide some form of alarm or alert through the vehicle controls or to operate the vehicle to bring it into a safe condition.

Figure 3:
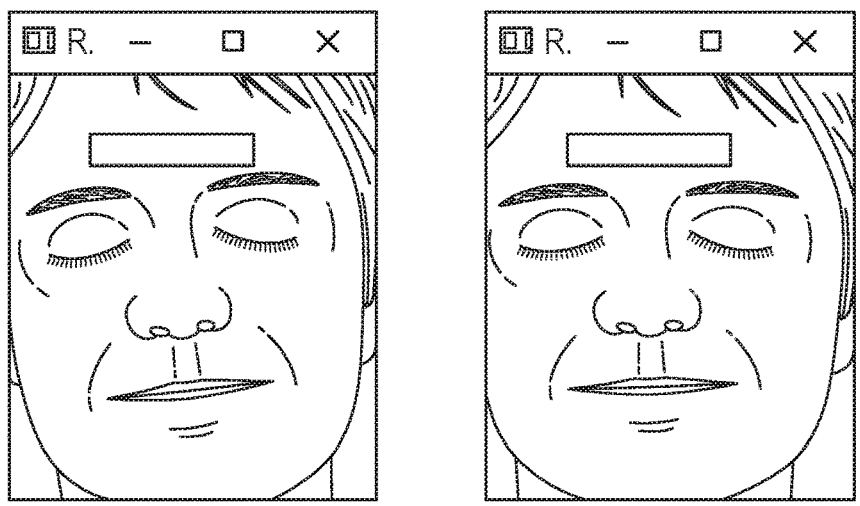
FIG. 3 illustrates two image frames from a motion-compensated video image.

The analysis of the video image by the image processor 10 to obtain a PPG signal relies upon analysing the image in a skin region of the subject 1. This is achieved by locating one or more areas in each video image frame which are images of the subject's skin and defining one or more regions of interest in such skin regions. Such regions of interest are usually square or rectangular and FIG. 3 illustrates two image frames from a video image with a region of interest shown on the forehead of the subject as a white rectangle. Because the operator of the vehicle is subject to the vehicle's movements, the subject moves considerably within the field of view of the camera and so appears in different positions in each frame of the image. In order to obtain a good PPG signal it is necessary for the region of interest to remain consistently positioned on the subject. Therefore it is normal to perform an image registration process on the video image so that the subject appears to remain still, while the background moves. Such image registration processes are well-known.

For each pair of adjacent frames, the image registration process involves the application of the projective transformation to the second frame, that minimizes the differences between the overlapping region of the second frame and a pre-specified sub-region of the first frame. Each such projective transformation can be specified as a set of 8 parameters, with $t_{ni}$ taken to denote the value of the $i^{th}$ such parameter corresponding to the transformation between the $n-1^{th}$ and $n^{th}$ frame. For n=1 no such transformation exists, with the instead set to zero, for all i. The cumulative transformation at frame n is defined as the sum of the transformations up to that frame:

$$T_{ni} = \Sigma_{m=1}^{n} t_{mi}$$

The motion transformations can be applied to the video images to produce a set of motion-compensated video images in which the subject remains apparently still, but the background appears to move. This allows the region of interest to be positioned at the same position in each frame and thus to represent the same area of skin of the subject throughout the video image.

However, as mentioned above, if the subject is in a non-uniform illumination field, then although the image registration process corrects the images for movement, the variation in illumination on the face of the subject will still be present. Thus the brightness of the subject will appear to flicker or vary and such a variation in illumination is a significant source of noise for the PPG signal analysis.

In accordance with the invention, therefore, after the image registration process, the calculated motion transformation is used to form an illumination model of how the illumination on the face has changed because of the motion of the subject relative to the camera. The difference between the modeled illumination and the intensity variation detected in the region of interest on the skin should then have a clearer PPG component. Conventional methods for estimating the vital signs of the subject, such as heart rate or breathing rate from the signal will then produce a better estimate because of the reduction of noise from varying illumination.

Figure 4:
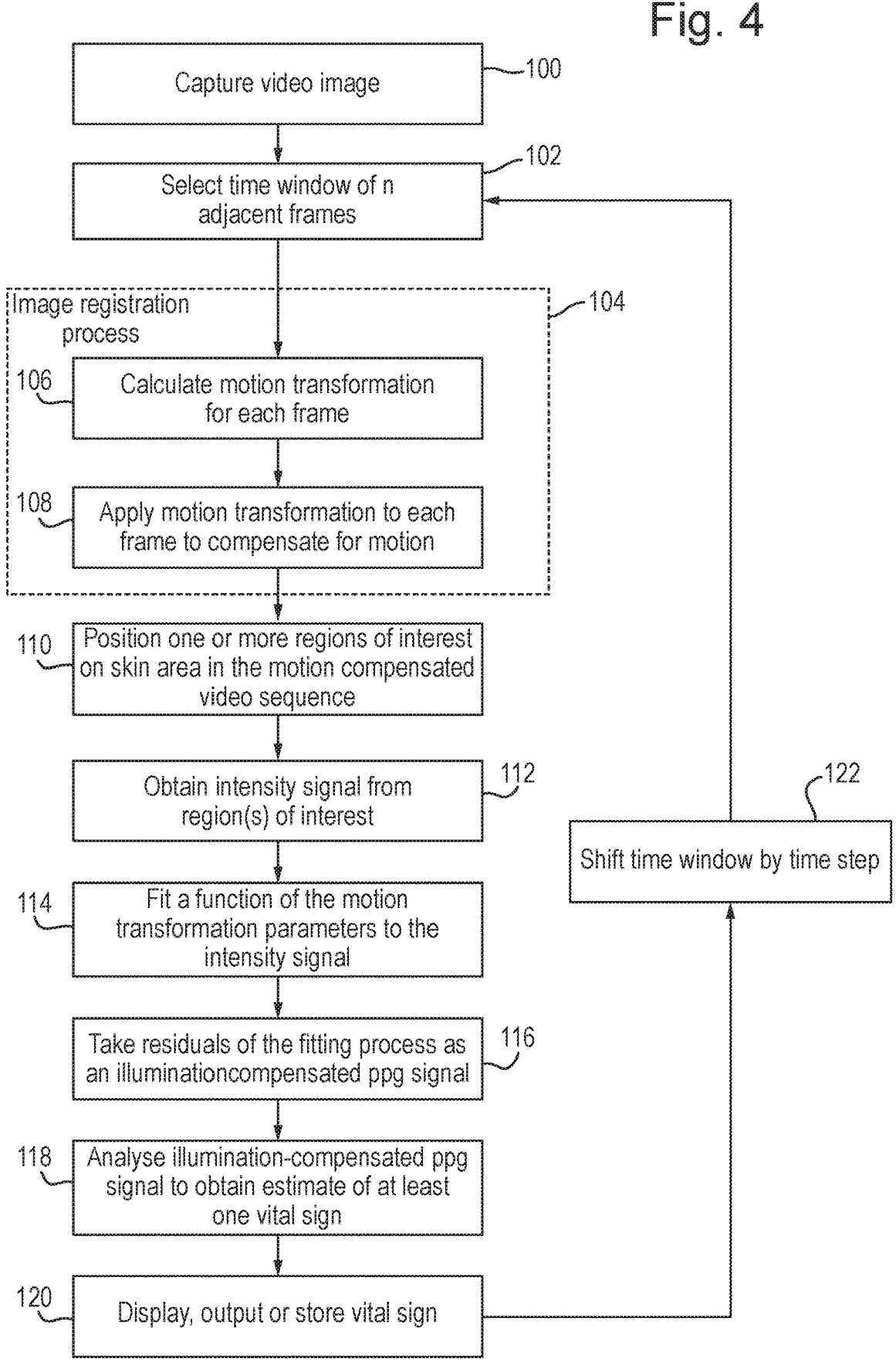
FIG. 4 is a flow diagram of one embodiment of the invention.

One embodiment of the method is shown in more detail in FIG. 4.

In step 100 a video image consisting of successive image frames is captured and in step 102 a time window of n adjacent frames is selected (for example n may be 200). Then in step 104 a conventional image registration process is executed. This process involves calculating in step 106 a motion transformation representing the movement of the subject between adjacent image frames of the video image and in step 108 this transformation is used to compensate the video images for the subject motion to place the subject in the same position in each frame.

In step 110 one or more regions of interest on skin areas of the subject in the motion-compensated video image are defined and in step 112 an intensity-representative signal is obtained from the region or each region of interest. Such signals may be obtained by averaging or summing the pixel values in the region of interest and this may be conducted on a single monochrome or colour channel or on a function, such as a ratio, of multiple colour channels of a video signal.

In step 114 the motion transformation calculated in step 106 is used to form an illumination model of how the illumination on the subject has changed as a result of the subject's movement. One example of such an illumination model is a linear combination of the cumulative transformation parameters, that is to say, each parameter is multiplied by a coefficient and added together.

$$\text{Illumination } L_n = k_0 + \Sigma_i k_i T_{ni}$$

The coefficients $k_0, k_1, \ldots, k_8$ are obtained through the minimization of $\Sigma_n (I_n - L_n)^2$, where $I_n$ is the mean intensity of the or each region of interest in the $n^{th}$ transformed frame.

Rather than a simple linear function, a higher-order function such as a quadratic function of the cumulative transformation parameters may be used:

$$\text{Illumination } L_n = k_0 + \Sigma_i k_i T_{ni} + \Sigma_i k_{(i+8)} (T_{ni})^2$$

Once the illumination model has been fitted to the intensity signal, the residuals, i.e. the remaining differences between the fitted function and the intensity signal can be taken as a new residuals signal which still includes the PPG signal. The PPG signal will be stronger in this residuals signal because the main variations in illumination resulting from the subject's movement have been removed. In step 116 these residuals are taken as an illumination-compensated signal, one for each region of interest. In step 118 any of the known techniques for analysing a video image signal to derive a PPG signal may be applied to the illumination-compensated residuals signal(s) to derive an estimate of a vital sign such as heart rate or breathing rate. Where there are plural regions of interest, this may involve combining the illumination-compensated residuals signal(s) and then analysing the result to find the PPG signal and a vital sign estimate, or analysing them individually and combining the resulting estimates. In step 120 the estimated vital sign may be displayed and/or output and/or stored. Possible actions based on the vital sign are alarming or alerting the operator if the vital signs are abnormal or executing some control of the vehicle.

In step 122 the time window of n frames is shifted by a time step, such as one second, to obtain a new time window of n frames and the process is repeated to obtain a new vital sign estimate.

Figure 5:
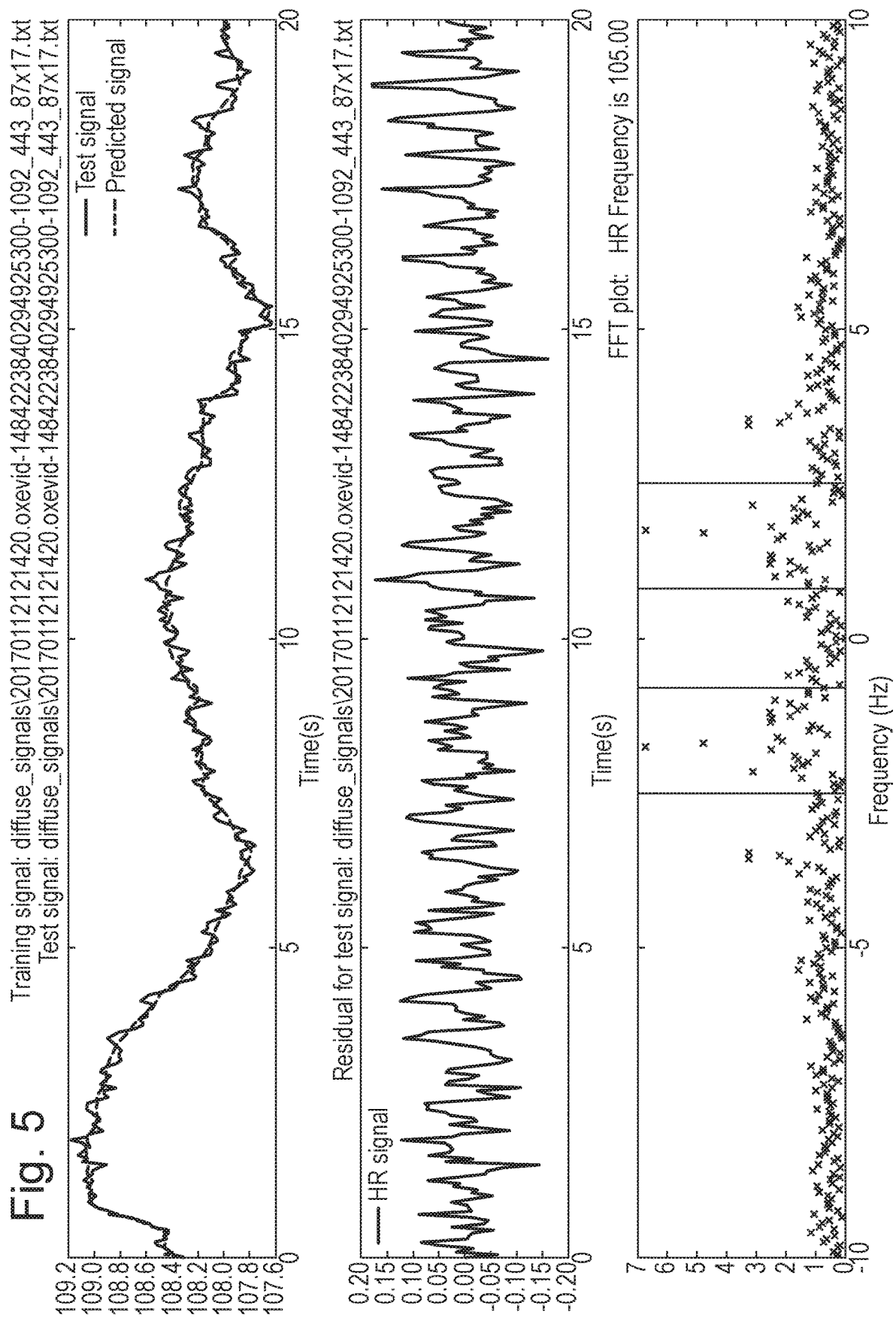
FIG. 5 shows the results of applying the method of an embodiment of the invention to a 20 seconds segment of video

FIG. 5 illustrates the results of applying the first embodiment of the invention to a video image sequence of a subject under spatially variable illumination. The top plot in FIG. 5 shows the original motion-compensated intensity signal in blue (solid) and the predicted illumination formed by fitting a quadratic function of the motion cumulative transform parameters to that intensity signal. The residuals, i.e. the difference between the two, is illustrated in the middle plot and this forms an illumination-compensated signal which includes a PPG component. The bottom plot shows a Fast Fourier Transform (FFT) analysis of that signal with the realistic physiological frequency bands for heart rate illustrated between the two pairs of vertical lines. The FFT representation of the residuals in the bottom plot shows strong signals in the two physiologically-possible ranges for heart beat.

Figure 6:
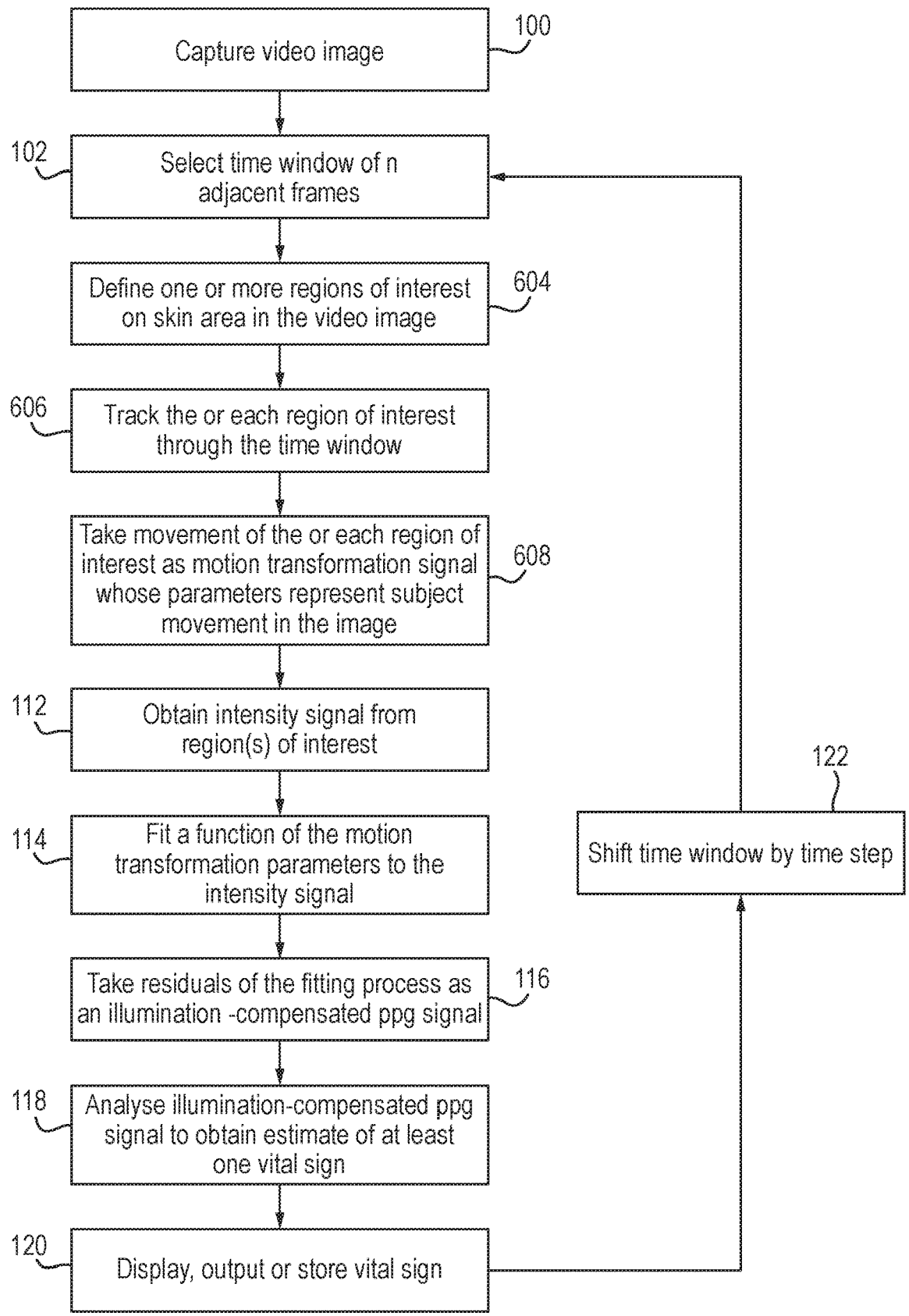
FIG. 6 is a flow diagram of an alternative embodiment of the invention.

FIG. 6 schematically illustrates an alternative embodiment of the invention in which instead of motion correcting the image and then defining the region of interest, the region of interest is defined first and then tracked through the video image, its movement representing the movement of the subject and thus providing the motion transformation signal and motion transformation parameters. As illustrated in FIG. 6, in step 102 a time window of n adjacent frames of the video image captured in step 100 is selected and in step 604 one or more regions of interest are defined on a skin area of the subject in the image. One automatic way of defining such regions of interest will be described below with reference to FIGS. 7 and 8, but other ways, such as detecting areas of skin by their colour or by recognising human shapes in the image are known and explained in the art. Having defined one or more regions of interest, the position of the or each region of interest is tracked through the time window in step 606 and in step 608 the movement is taken as the motion transformation signal whose parameters represent subject movement in the image.

In step 112 an intensity signal is obtained from the or each region of interest in the same way as in the first embodiment, for example by averaging or summing the pixel values in the region of interest, and then the method proceeds as in the first embodiment by fitting a function of the motion transformation parameters to the intensity signal for the or each region of interest and taking the residuals of the fitting process as an illumination-compensated PPG signal (step 116). This illumination-compensated PPG signal is analysed in step 118 to obtain an estimate of at least one vital sign, which is displayed and output or stored in step 120. The process then moves the time window by a time step, for example one second in step 122 and repeats. FIG. 8 illustrates in more detail the signal processing for one way of defining regions of interest and obtaining intensity and motion transformation signals of steps 604, 606, 608 and 112. Optionally firstly, in step 800, the average frame intensity of each frame is set to a constant value to reduce image flicker, e.g. by multiplying each pixel value by the mean pixel value over the whole sequence and dividing by a constant to scale the values as desired (e.g. 0-255 for 8 bit values).

In step 801, feature points in the video sequence are detected. There are many ways of detecting feature points in a video sequence using off-the-shelf video processing algorithms. For example, feature points consisting of recognisable geometrical shapes such as corner or edges can be detected based, for example, on the gradient of intensity variation in one or two dimensions, and any such conventional algorithm which identifies image feature points can be used in this invention. The feature points are tracked through the whole batch of video frames under consideration, e.g. by using a conventional tracking algorithm such as KLT tracking, to form "tracks" consisting of the x and y coordinates of each feature point in each image frame through the sequence.

In step 803 a time window (e.g. 9 seconds=180 frames at twenty frames per second) is taken. Thus the next steps of the process are conducted on a time window of the video sequence, and then the process will be repeated for another time window shifted along by some time increment. The successive windows may overlap, for example if a nine second window is stepped forwards by one second each time the overlap will be eight seconds.

Any tracks which do not exist in all the frames of the window are discarded.

In step 806, the central frame of the time window is taken and Delaunay triangulation is performed on the feature points. Delaunay triangulation is a process which creates triangles favouring large internal angles. FIG. 7(A) illustrates schematically three successive frames at times n−1, n and n+1 with the central frame n having five feature points 20 connected to form triangles. As can be seen in FIG. 7(A), the position of the feature points varies from frame-to-frame. Having formed the triangles in the central frame of the sequence, the same triangles are formed in each other frame of the sequence (i.e. the same feature points are connected together) so that each triangle is defined throughout the whole nine second time window by three KLT tracks specifying the positions of its vertices. In step 808, the in-circle 22 of each triangle is formed and then a square 24 concentric with the in-circle 22 is formed, aligned with the x and y axes of the image frame and with a side length equal to the diameter of the in-circle. Each of these squares 24 then constitutes a region of interest from which a signal will be obtained for further processing.

As illustrated in step 810 the intensity in each region of interest in each frame is calculated (the sum of all the pixel intensity values) and the intensity for each square region of interest (ROI) through the time window corresponds to a signal (i1 to im) to be processed. In visible light, for a camera outputting three R, G, B colour channels, only the green channel is used. However if the scene is illuminated by infra-red light, the mean of the three colour channels is used. The image intensity of each ROI through the frame sequence will typically vary as schematically illustrated in FIG. 7(B). The location (x, y) of each region of interest (for example the centre or a specified corner of each square) is also obtained and represents the movement of the subject. The intensity signals and movements of each region of interest are then output as time signals as illustrated in step 112.

The intensity and movement signals output from the process of FIG. 8 are input to step 114 of FIG. 6.

The invention claimed is:

1. A method of processing sequence of image frames forming a video image of a human subject to estimate a vital sign of the subject comprising the steps of:
   analysing the video image to obtain a motion transformation whose parameters represent the movement of the subject;
   defining at least one region of interest on the subject in the video image and obtaining a signal representing the image intensity in the at least one region of interest;
   obtaining a predicted illumination signal by fitting a function of the motion transformation parameters to the signal representing the image intensity;
   obtaining a residuals signal representing the difference between the signal representing the image intensity and the predicted illumination signal after said fitting; and
   analysing the residuals signal to obtain an estimate of at least one vital sign of the subject.

2. A method according to claim 1 wherein the step of analysing the video image to obtain a motion transformation comprises performing a motion correction process which produces a motion corrected video image and the motion transformation.

3. A method according to claim 1 wherein the step of analysing the video image to obtain a motion transformation comprises performing an image registration process.

4. A method according to claim 1 wherein the region of interest is defined in the video image before the step of analysing the video image to obtain a motion transformation, and the step of analysing the video image to obtain a motion transformation comprises tracking the region of interest through the sequence of image frames.

5. A method according to claim 1 wherein the motion transformation is a projective transformation.

6. A method according to any claim 1 wherein the step of fitting a function of the motion transformation parameters to the signal representing the image intensity comprises linear or quadratic regression.

7. A method according to claim 1 wherein a plurality of regions of interest are defined on the subject.

8. A method according to claim 1 wherein the intensity signal is formed for the or each at least one region of interest by averaging or summing pixel values in the at least one region of interest.

9. A method according to claim 1 wherein the intensity signal contains a photoplethysmographic signal.

10. A method according to claim 1 wherein the video image is of a subject in a vehicle.

11. Apparatus for video image processing comprising an input for receiving a video image signal, an image processor adapted to process a video image in accordance with the method of claim 1, and an output for outputting the estimate of the at least one vital sign of the subject.

12. A video monitoring system comprising a video camera for capturing a video image of a subject and outputting a video image and apparatus for video image processing as defined in claim 11.

13. A vehicle having installed therein a video monitoring system according to claim 12, the video camera being positioned to capture an image of the operator of the vehicle.

* * * * *